US009361810B2

(12) United States Patent
Brumley et al.

(10) Patent No.: US 9,361,810 B2
(45) Date of Patent: Jun. 7, 2016

(54) UNINHABITED TEST CITY

(75) Inventors: Robert H. Brumley, Weems, VA (US);
Robert H. Brumley, III, Richmond, VA (US); Michael J. Reedy, Kingsport, TN (US); Fletcher W. Brumley, London (GB); Charles Warner, Washington, DC (US)

(73) Assignee: PEGASUS GLOBAL STRATEGIC SOLUTIONS LLC, Reston, VA (US)

( * ) Notice: Subject to any disclaimer, the term of this patent is extended or adjusted under 35 U.S.C. 154(b) by 628 days.

(21) Appl. No.: 13/436,531

(22) Filed: Mar. 30, 2012

(65) Prior Publication Data

US 2013/0255405 A1    Oct. 3, 2013

(51) Int. Cl.
*G06F 17/50* (2006.01)
*G09B 25/04* (2006.01)
*G01N 37/00* (2006.01)

(52) U.S. Cl.
CPC ............... *G09B 25/04* (2013.01); *G01N 37/00* (2013.01)

(58) Field of Classification Search
CPC .... G01N 37/00; G09B 25/04; G06F 17/5004; G06F 17/5018
USPC ............................................................ 703/1
See application file for complete search history.

(56) References Cited

U.S. PATENT DOCUMENTS

| 3,991,485 | A | 11/1976 | Golenski | 35/11 |
| 5,103,600 | A | 4/1992 | Geiger et al. | 52/6 |
| 8,000,897 | B2* | 8/2011 | Breed | B60N 2/2863 701/301 |
| 8,774,950 | B2* | 7/2014 | Kelly | G05B 23/0267 700/65 |

| 2003/0058103 | A1 | 3/2003 | Jansson | 340/540 |
| 2003/0227440 | A1 | 12/2003 | Fager et al. | 345/156 |
| 2006/0027133 | A1* | 2/2006 | Suematsu | 104/27 |
| 2009/0070131 | A1* | 3/2009 | Chen | 705/1 |
| 2009/0243914 | A1* | 10/2009 | Song et al. | 342/169 |
| 2010/0263295 | A1* | 10/2010 | Flanagan | 52/1 |

FOREIGN PATENT DOCUMENTS

| ES | 2 076 864 | 11/1995 |
| FR | 2 953 235 | 6/2011 |
| WO | WO 2009/126173 | 10/2009 |
| WO | WO 2013/149232 | 10/2013 |

OTHER PUBLICATIONS

Nghiem et al. (Observations of urban and suburban environments with global satelite scatterometer data, (2009), 14 pages).*
Zhao et al., "Increasing Gross Primary Production (GPP) in the Urbanizing Landscapes of Southeastern Michigan", *Photogrammetric Engineering & Remote Sensing*, vol. 73, No. 10, Oct. 2007, pp. 1159-1167.

* cited by examiner

*Primary Examiner* — Kamini S Shah
*Assistant Examiner* — Andre Pierre Louis
(74) *Attorney, Agent, or Firm* — Pillsbury Winthrop Shaw Pittman LLP

(57) ABSTRACT

A full scale uninhabited test facility is configured for building modular man made structures, evaluating modular man made structures, evaluating use of modular man made structures, and/or for other purposes. The structures may be located in a user configurable simulated environment. One or more structures may be configured to simulate use by inhabitants in a simulated environment. After testing, the constructed structure(s) may remain where built in the simulated environment(s) until such time as another user may reconfigure the environments or structures. As additional structures are built and/or modified, new and old structures may operate side by side, generating opportunity, for example, to test new and/or different technology on the same structures.

22 Claims, 14 Drawing Sheets

UNINHABITED TEST CITY

FIELD

The disclosure relates to a full scale, fully integrated, cross-disciplinary, uninhabited test, evaluation, and/or certification facility configured for simulating use of, and/or evaluating, man made structures in a real world simulated environment.

BACKGROUND

Typically, full scale simulation, evaluation, and/or testing is conducted in the perfection and singularity of a laboratory. Simulation may be conducted on only one structure at a time. Monitoring during testing may be rudimentary and/or the simulated structure may be disassembled or torn down after testing. For example, in an effort to improve the performance of a structure during an earthquake, a full scale building may be constructed in a university earthquake lab (indoors). The structure undergoes a simulated earthquake while forces are monitored in the structural members of the building. After the test the building is manually checked for damage. The building may be torn down and rebuilt multiple times for multiple earthquake simulations.

Industry sector focused centers of excellence are typically centered around one industry sector (e.g., energy, defense, transportation, biomedical, etc.). Testing, evaluation and/or certification occurring in these research environments is normally not cross disciplinary, typically occurs in a pristine lab environment, and is not conducted at full scale.

Full scale structural simulation outside a laboratory setting is often for the purpose of television/film production. Structures for television/film production are built to simulate common settings such as a home, an office, a school, and/or other settings. However, structures built for television/film production are only partial structures and do not comprise a full simulation of an actual structure. For example, a structure may have no exterior walls, a structure may contain no working appliances, a structure may not be connected to plumbing, etc. Also, structures built for television/film production are not monitored for experimental reasons. They do not contain sensors, wiring, processors, and/or other equipment for monitoring performance of the structure during simulation.

Full scale structural simulation may also be used by the military for training purposes. Structures built for training purposes are typically only partial structures and do not comprise full simulation of an actual structure. Often the structures are a façade, and/or exterior walls only and contain no interior detail. If a simulated structure is monitored by the military, it is typically monitored for the performance of military, not the performance of structure.

SUMMARY

The present disclosure relates to a full scale, fully integrated, cross-disciplinary, uninhabited test, evaluation, and/or certification facility configured for simulating use of, and/or evaluating, man made structures in a real world simulated environment. The facility may be configured to simulate multiple aspects of a typical community with a fully operating infrastructure sufficient to support a typical community. The facility may be configured for training, operational testing, technical testing, and/or for other purposes. Testing may comprise destructive and/or non-destructive testing.

The facility may comprise a proving ground configured to test structures related to one or more user applications including, for example, intelligent transportation systems, alternative energy (e.g. wind, solar), power generation, smart grid technologies, telecommunications, resource development (e.g., desalinization), security (e.g., physical security, cyber security), and/or other applications. The test facility may provide testing and/or evaluation capability that is integrated with other on-going activities in a system of systems context. New technologies may be introduced, tested, and measured in a cross-disciplinary, imperfect, operating, functioning, legacy environment, outside the limited scale of a laboratory or research facility. Researchers may be able to assess technical test capabilities and/or methodology gaps. Researchers may be able to characterize performance and/or validate the design of a system (and/or a system of systems) in one or more simulated environments. Prior to commercialization, researchers may be able to better understand the impact of the new technology over an entire economy, rather than just a specific sector.

As such, one aspect of the disclosure relates to a full scale uninhabited test facility. The test facility may be configured for building modular man made structures, evaluating modular man made structures, evaluating use of modular made structures, and/or for other purposes. The structures may be located in a user configurable simulated environment. One or more structures may be configured to simulate use by inhabitants in a simulated environment. The test facility may comprise one or more of a user configurable simulated environment, structures, a user interface, sensors, a processor, a monitoring facility, and/or other components.

The description of the functionality of the test facility provided by the term "uninhabited" is not intended to be limiting, as habitation may be necessary for operation of the test facility and/or for other purposes. For example, it may be necessary for a facility fire department to establish a residence in the test facility because the fire department may be required to operate in shifts 24 hours a day, seven days a week, for safety reasons.

Examples of user configurable simulated environments may comprise an urban environment, a suburban environment, a rural environment, and/or other environments. User configurable environments may be configured to simulate infrastructure and/or structures in an environment. Simulated density of buildings, telecommunications infrastructure, transportation infrastructure, public utilities infrastructure and/or other infrastructure may decrease moving from urban, to suburban, to rural. Open space may increase moving from urban, to suburban, to rural.

The user configured environments may be geographically arranged to simulate transitions from one environment to another. For example, placing a suburban environment between an urban environment and a rural environment may simulate a transition from urban to suburban and a transition from suburban to rural.

The density of structures in an environment may comprise the combined interior square footage of structures per given land area. The interior square footage of structures in a given land area may vary with structure height and/or the number of floors per structure, the distance between structures, and the structure foot print (width×depth). Structure dimensions (e.g., height, width, and/or depth) may vary from one structure to the next. The structure density may vary geographically within a single environment, and/or regionally across the urban, suburban, and/or rural environments of the test facility.

Structure height may be more variable in an urban environment compared to in a suburban environment and/or in a rural environment. The man made structures in an urban environment may comprise one or more low rise structures and/or one or more high rise structures. The structures in the suburban and/or rural environments may comprise one or more low rise structures. For example, the urban environment may comprise multiple high-rise office buildings, multiple high rise apartment buildings, and/or one or more low rise restaurants. The rural environment may comprise a single one floor farmhouse.

Modular man made structures may comprise, for example, one or more of a home, an office building, an apartment building, a street, a highway, a bridge, an airport, a power plant, and/or other structures. A user may evaluate a structure by choosing an existing environment(s) or configuring environment(s) to user requirements. The user may reconfigure an existing structure(s) and/or build new structure(s) in the user's chosen environment(s). The modular structures may be configured for relocation, remodeling the existing structure, connection to present and/or future construction, future testing, reconfiguring structure monitoring and control capabilities, and/or other reconfiguration. Modularity may also comprise pre-installation of utilities in undeveloped areas of the test facility.

A user may input simulation and/or other information via the user interface. The test facility may simulate full scale use of structure(s) in one or more user configured environments based the input information. Input from user may include, for example, calculation algorithms, fictional weather conditions, time of day, geographic location, the people and/or entity interacting with the structure, the size of entity and/or the number of people interacting with a structure, biographical information about the people interacting with a structure, and/or other input information.

One or more sensors may be positioned throughout the test facility. The sensors may be configured to generate one or more output signals conveying information related to ambient conditions in and/or around man made structures, control parameters, structure performance, and/or other parameters. Output signals generated by the sensors may be utilized for one or more of deriving an algorithm, obtaining data to test a hypothesis, returning response information in a control loop feedback mechanism (e.g., a PID controller), monitoring a specific variable relative to threshold level(s), and/or other purposes.

The processor may be configured to execute one or more computer program modules. The one or more computer program modules may obtain input information and/or regulate one or more control parameters responsive to the input information. The input information may be obtained responsive to one or more inputs made by the user via the user interface, output information from the sensor(s), and/or other sources. The regulated control parameters may be calculated based on a simulation algorithm selected, uploaded, and/or programmed by the user via the user interface. The processor modules may comprise an input parameter module, a calculation module, a parameter regulation module and/or other modules.

The one or more input parameters obtained by the input parameter module may comprise, for example, ambient conditions, fictional weather conditions, time of day, geographic location, the people and/or entity interacting with the structure, the size of entity and/or the number of people interacting with a structure, biographical information about the people interacting with a structure, and/or other input parameters.

The calculation module may be configured to calculate, responsive to the information obtained by the input parameter module, (i) facility wide control parameters, and (ii) structure specific component control parameters. The calculated parameter information may comprise outputs from the calculation module.

The structure specific component control parameters may be calculated stochastically for each individual structure. For example, the calculation module may receive input information from the input parameter module describing an urban population with a specific set of demographics entered by a user via the user interface. Responsive to the input information, the calculation module may calculate water use per day for the entire population (a facility wide control parameter). The calculation module may also stochastically calculate the fraction of the water used by each individual structure in the urban environment (a structure specific component control parameter).

The parameter regulation module may be configured to regulate facility wide and/or structure component control parameters based on output from the calculation module. The parameter regulation module may output command signals configured to regulate the operation of facility wide and/or individual structure components. Continuing with the example above, based on results of the stochastic fractional water use calculation, the parameter regulation module may output command signals to coordinate operation of sinks, showers, toilets and/or other water using components across the entire facility and/or in an individual structure.

A user may gather data during and/or after simulation without interrupting or influencing the simulation via the monitoring facility. The monitoring facility may be configured to allow monitoring of user configured simulated environments, and/or the simulated use of man made structures. The monitoring facility may comprise one or more above ground monitoring campuses located away from the simulated environment(s), and/or an underground monitoring facility located underground below the simulated environment(s).

After testing, the constructed structure(s) may remain where built in the simulated environment(s) until such time as another user may reconfigure the environments or structures. As additional structures are built and/or modified, new and old structures may operate side by side, generating opportunity, for example, to test new and/or different technology on the same structures.

These and other objects, features, and characteristics of the system or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a", "an", and "the" include plural referents unless the context clearly dictates otherwise.

DETAILED DESCRIPTION

Figure 1:
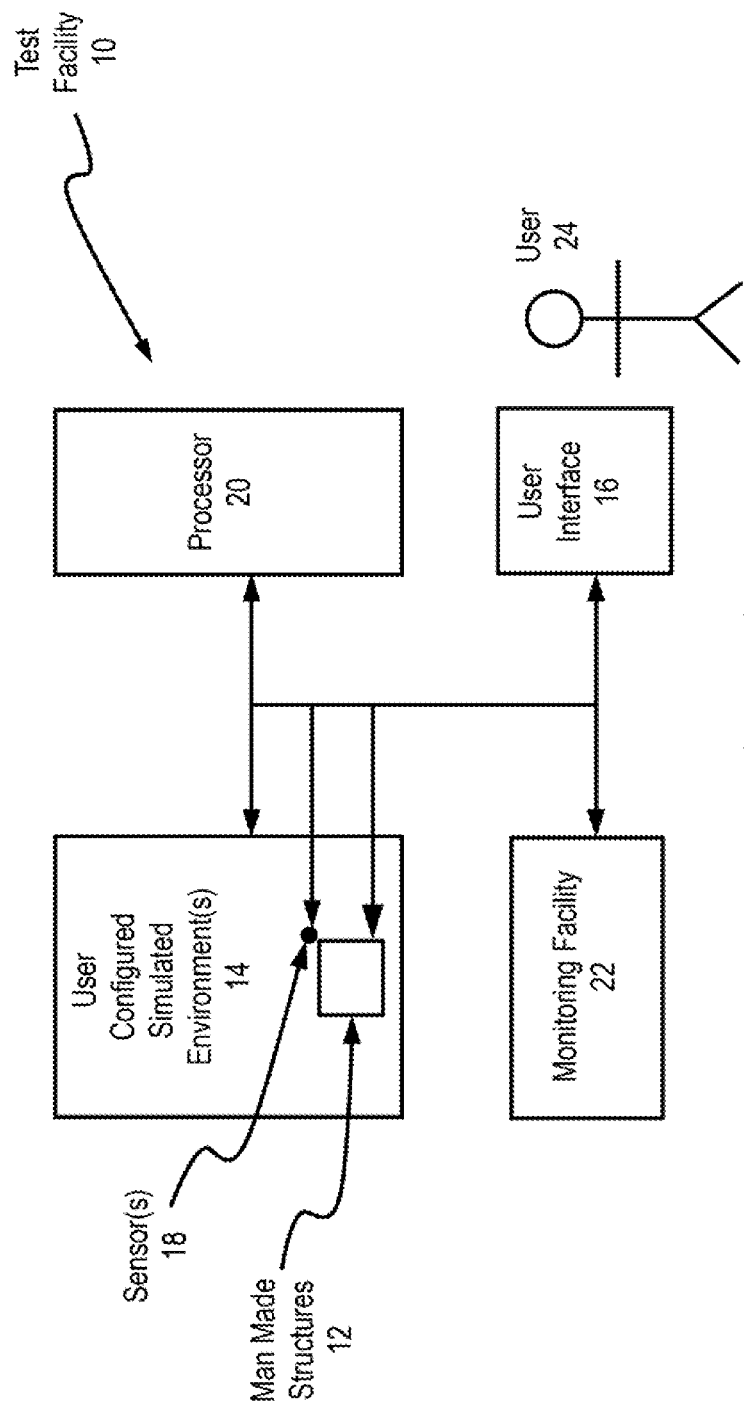
FIG. 1 is a schematic representation of the components of a full scale uninhabited test facility.

FIG. 1 schematically illustrates a full scale uninhabited test facility 10 configured to simulate a typical community (e.g., approximately 20 square miles in size with a population of approximately 35,000 people). Test facility 10 may be configured with a physical infrastructure representative of an urban footprint (e.g., high rise structures, urban canyons), suburban neighborhoods (e.g., mixed structure types, and neighborhood design), rural areas (e.g., rural residences, farms, ranches), open spaces (e.g., for expansion and/or isolated testing areas with unique designs), a road network (e.g., interstate highway, urban streets, rural roads), a ubiquitous wireless and fixed line communications infrastructure, and/or other physical infrastructure.

Test facility 10 may be configured to simulate the day to day technology and economic activity of the real world as closely as possible. Test facility 10 may be configured to allow one or more users to develop, test, and/or implement new and/or existing technology at full scale, allowing the one or more users to better understand all aspects (anticipated and/or unanticipated) of the technological impact of the technology.

Full scale uninhabited test facility 10 may be configured for building modular man made structures 12, evaluating modular man made structures 12, evaluating use of modular made structures 12, and/or for other purposes. The facility may comprise one or more of a user configurable simulated environment 14, structure(s) 12, a user interface 16, sensors 18, a processor 20, a monitoring facility 22, and/or other components. Test facility 10 may comprise one or more user configurable structures 12 configured to simulate use by inhabitants in environments 14.

Structures 12 may comprise, for example, one or more of a home, an office building, a warehouse, an apartment building, a street, a highway, a bridge, an airport, a power plant, a prison compound, signage (e.g., electric and/or billboards), fences, walls, a device (e.g., a security camera), a system of devices (e.g. a telecommunications network), and/or other structures. Structures 12 may be controlled by software programs. Software programming may also be tested in test facility 10. Structures 12 may comprise attached and closely spaced inner-city structures, high-rise structures, attached houses, closely spaced industrial and/or storage structures, apartment buildings, detached houses, widely spaced industrial and/or storage structures, and/or other structures. Structures 12 may be built with a layout and/or features such as stairs, elevators, basements, ventilation ducts, fireplaces, chimneys, etc. that would be typical for the specific type of structure. Furniture, artwork, decorations, landscaping, and/or other static features of a typical structure may be placed within/on/around structures 12 as appropriate.

Structures 12 may be built with common and/or experimental construction practices from one or more construction materials (e.g., wood, brick, masonry, metal, concrete, re-enforced concrete, stucco, tiles, shingles, glass, etc.). Structures 12 may be constructed to closely simulate typical real world structures. For example, walls of a home built in test facility 10 may be framed with wood, built with plumbing, power lines, and or insulation in the walls, and finished with plastered and/or painted drywall.

In some implementations, a user 24 may evaluate structures 12 by choosing an existing environment(s) 14 or configuring environment(s) 14 to user requirements. User 24 may reconfigure an existing structure(s) 12 and/or build new structure(s) 12 in one or more locations throughout chosen environment(s) 14. Test facility 10 may simulate full scale use of structure(s) 12 in environments 14 as configured by user 24 based on input from user 24 via user interface 16. Input from user 24 may include, for example, fictional weather conditions, time of day, geographic location, the people and/or entity interacting with the structure, the size of entity and/or the number of people interacting with a structure, biographical information about the people interacting with a structure, and/or other input information.

Simulated use of structure(s) 12 (test facility 10 application areas) may comprise, for example, testing telecommunications infrastructure (e.g., in urban canyons), simulating biohazard transport through a city, testing intelligent transportation system technologies, simulating resource development (e.g., desalinization), testing security technology (e.g., testing security at a prison compound, cyber security, unmanned border patrols in rural areas, robotic bomb threat investigation), testing green energy technology (e.g., solar cell implementation, geothermal power generation, etc.), testing smart grid technology, testing traffic management technology (e.g., driverless cars), weapons testing, and/or other simulations. User 24 may gather data during/after simulation without interrupting or influencing the simulation.

Structures 12 and/or environments 14 may function as legacy infrastructure wherein, after testing, constructed structure(s) 12 may remain where built in environment(s) 14 until such time as another user may reconfigure environments 14 or structures 12. As additional structures are built and/or modified, new and old structures may operate side by side, generating opportunity, for example, to test new and/or different technology on the same structures 12.

Modular structures 12 may comprise reconfigurable structures configured for relocation, remodeling the existing structure, connection to present and/or future construction, future testing, reconfiguring structure monitoring and control capabilities, and/or other reconfiguration. For example, structure modularity may comprise ports external to the structure configured for one or more of connecting/disconnecting telecommunication and/or sensory equipment to the structure, connecting/disconnecting power to the structure, connecting/disconnecting water to the structure and/or other ports. In some implementations, structure modularity may comprise mechanical connection points configured for construction additions to the structure and/or the mechanical connection of one structure to another. Modularity may comprise pre-installation of utilities in undeveloped areas of the test facility, wherein pre-installed utilities may comprise one or more of water, power, electricity and/or other utilities. Modularity may comprise empty conduit, pre-dug trenching, and/or other features.

Uninhabited test facility 10 may comprise a facility where no person lives permanently in any simulated environment and/or man made structure used for testing. However, the description of the functionality of the test facility provided by the term "uninhabited" is not intended to be limiting, as habitation may be necessary for operation of the test facility and/or for other purposes. For example, it may be necessary for a facility security team and/or a facility fire department to establish residences in the test facility for meals and/or sleeping because the security team and/or fire department may be required to operate in shifts 24 hours a day, seven days a week, for safety reasons. The security team may, for example, need to monitor a security fence, closed circuit television, motion detectors, audio sensors, and/or other aspects of a security system installed around/throughout test facility 10.

Figure 2:
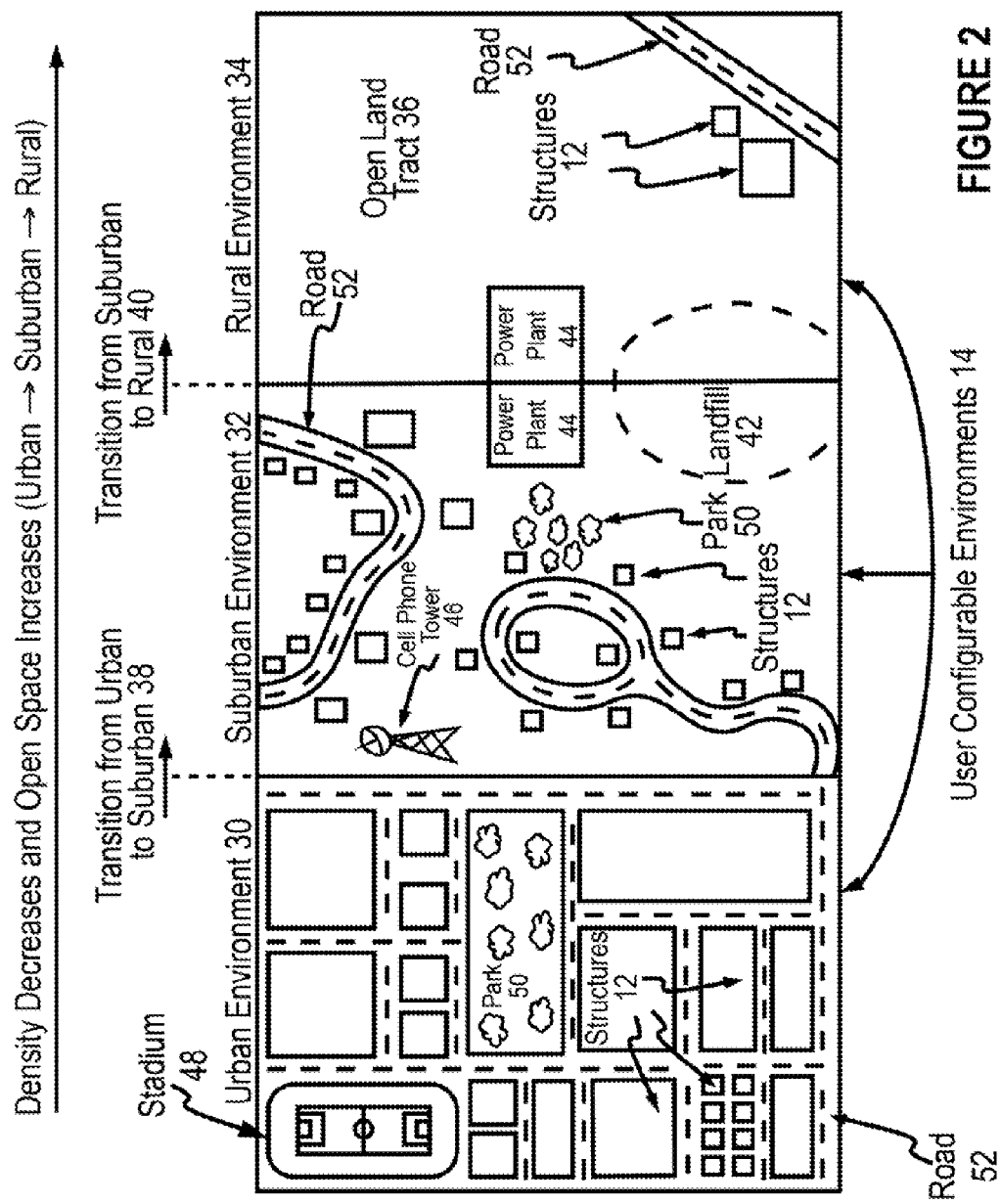
FIG. 2 is a description of the urban, suburban, and rural user configurable environments of the test facility.

FIG. 2 illustrates user configurable environments 14 that may be configured to simulate different settings. Man made structures 12 may be built in user configurable environments 14. User configurable environments may simulate use of man made structures in the simulated settings. User configurable environments 14 may comprise an urban environment 30 configured to simulate infrastructure and/or man made structures in a city, a suburban environment 32 configured to simulate infrastructure and/or man made structures around a city, a rural environment 34 configured to simulate infrastructure and/or man made structures in non urban or suburban areas, and/or other environments. Simulated density of buildings, roads, public utilities infrastructure and/or other infrastructure may decrease moving from urban environment 30, to suburban environment 32, to rural environment 34. Open space may increase moving from urban environment 30, to suburban environment 32, to rural environment 34.

Urban environment 30 may comprise an urban core, a commercial zone, an industrial zone, and/or other areas. The urban core may be configured to represent the mixed architectural typology found in a typical downtown setting and may be built from one or more construction materials as described above. One or more structures may be historical. One or more structures may be modern. The urban core may comprise landscaping, parking, sidewalks, street lights, service alleys, and/or other features that make up a typical city center. The commercial zone may be located adjacent to the urban core. The commercial zone may, for example, comprise one or more of a bank, a gas station/convenience store, a strip mall, town homes, and or other structures. The industrial zone may be located adjacent to the urban core. The industrial zone may be comprised of one or more warehouse structures with and/or without office space, that vary in height and/or form, and/or other structures. Parcels in the industrial zone may be configured with abundant pedestrian and vehicular circulation space provided.

Suburban environment 32 may include one or more fully functioning (utilities, appliances, etc. included and working) homes built on winding streets (simulating a typical suburban neighborhood) with street lighting, landscaping, sidewalks, and/or other features. One or more of the suburban homes in suburban environment 32 may be configured to simulate a typical suburban home with, for example, gabled roofs, two car garages, picket fencing, one or two stories, and/or other features.

Rural environment 34 may comprise irrigated farmland suitable for farming. Rural environment 34 may comprise farm houses, barn like structures, and/or other typical structures found in rural settings. Rural environment 34 may comprise one or more open land tracts 36. An open land tract may comprise an open area of land between man made structures. For example, an open area of land between man made structures may comprise one or more of farmland, land for grazing cattle, and/or undeveloped land containing no man made structures. Open land tracts 36 may comprise terrain variation (e.g., hills, flat areas, mountains), bodies of water, foliage/vegetation, and/or other features. Open land tracts 36 may comprise areas of different types of soil. For example, open land tracts 36 may comprise rolling sand dunes. Open land tracks 36 may comprise dirt suitable for farming.

The relative geographic position of urban environment 30, suburban environment 32, and/or rural environment 34 may be configured to simulate transitions between environments. For example, placing suburban environment 32 between urban environment 30 and rural environment 34 may simulate a transition from urban to suburban 38 and a transition from suburban to rural 40. In some implementations, suburban environment 32 and/or rural environment 34 may be arranged to radiate outward from a central urban environment 30 to mimic growth of a typical city. In some areas the transition between environments may be abrupt while in other areas the transition may be more gradual. The transition from urban to suburban may comprise city streets changing to suburban boulevards, decreasing building height, areas of primarily densely populated apartment buildings with few single family homes changing to areas of primarily single family homes with a few apartment buildings, and/or other transitions. The transition from suburban to rural may comprise suburban boulevards changing to two lane country roads (paved or dirt), suburban neighborhoods giving way to open land tracts, and/or other transitions.

Figure 3:
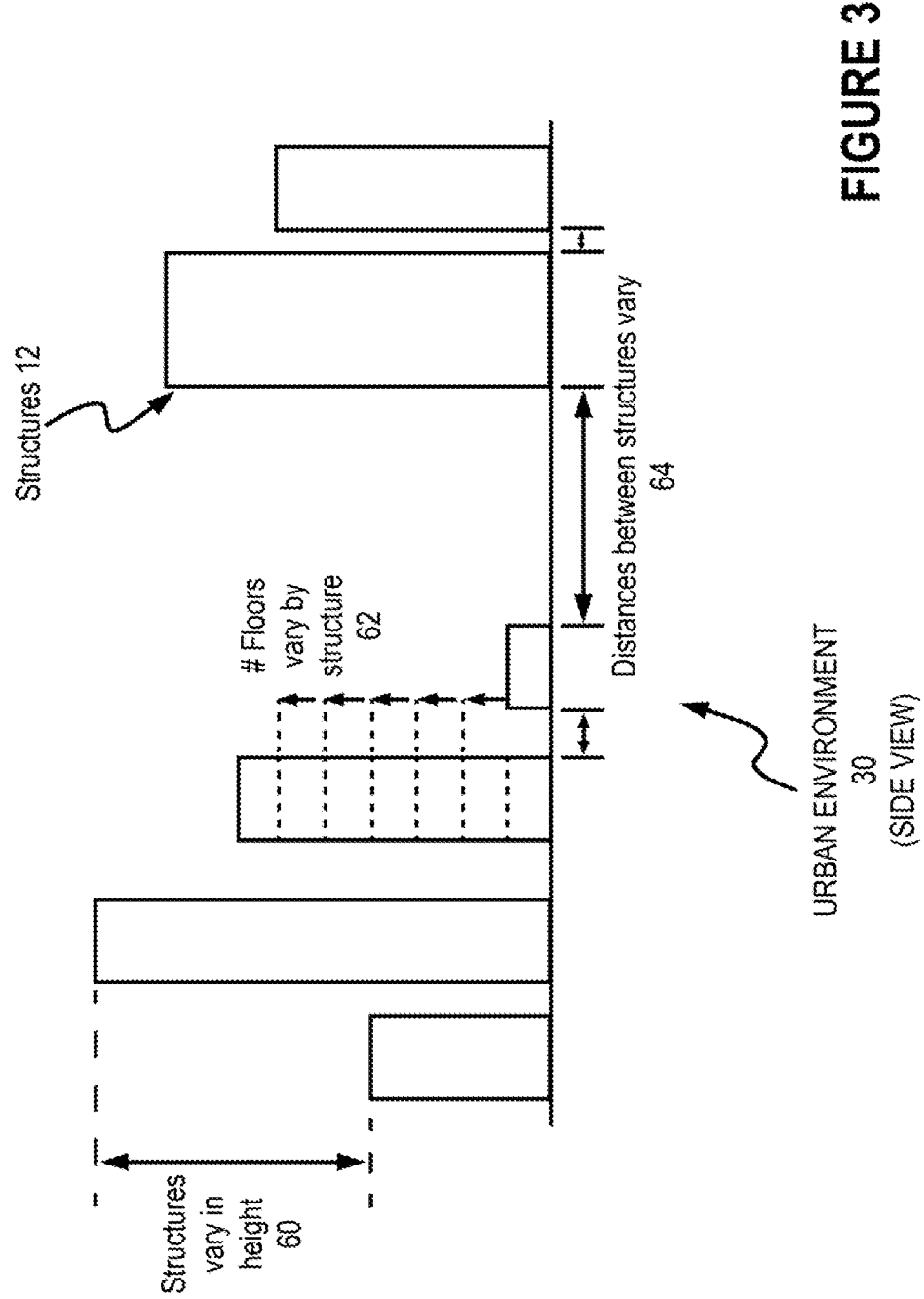
FIG. 3 is a description of structure height variation, variation of the distance between structures, and the variation of the number of floors in each structure.
Figure 4:
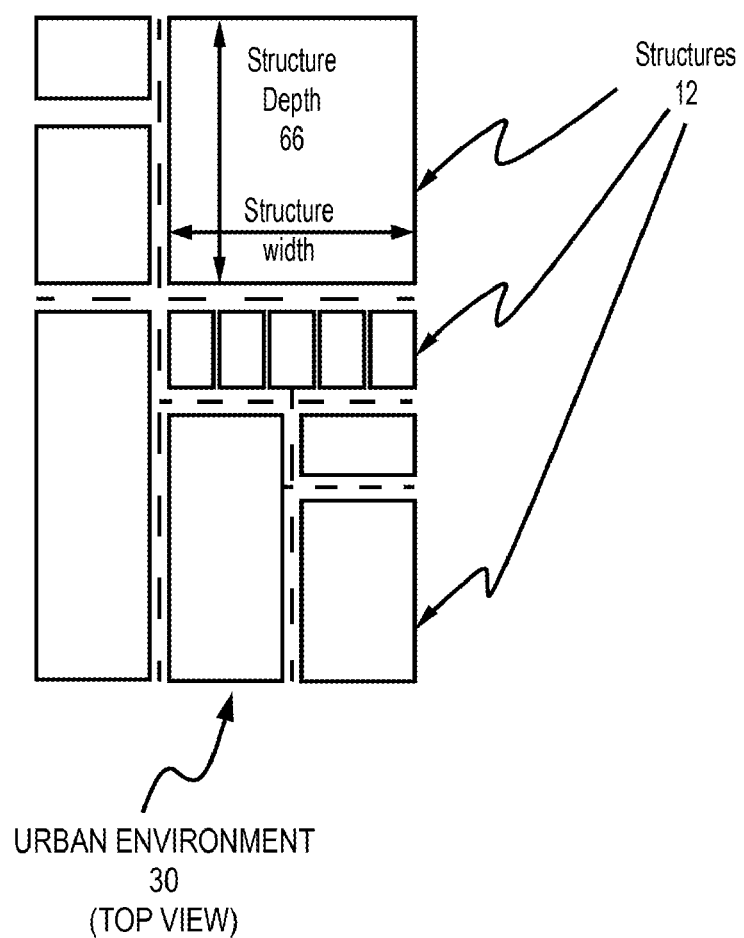
FIG. 4 is a description of a structure's footprint.

FIGS. 3 and 4 may illustrate density of man made structures 12 in urban environment 30. The density of structures in urban environment 30 may comprise the combined interior square footage of structures per given land area. The interior square footage of structures in a given land area may vary with (FIG. 3) structure height 60 and/or the number of floors per structure 62, the distance between structures 64, and (FIG. 4) the structure foot print (width×depth) 66. Structure dimensions (e.g., height, width, and/or depth) may vary from one structure to the next. Density of structures in urban environment 30 may be configured to create narrow alleyways to simulate urban canyons. Density of structures in suburban environment 32 (not shown) may be lower than the structural density of urban environment 30. Density of structures in rural environment 34 (not shown) may be lower than the structural density of suburban environment 32. The structure density may vary geographically within a single environment, and/or regionally across the urban, suburban, and/or rural environments of the test facility.

Structure height may be more variable in urban environment 30 compared to suburban environment 32 and/or rural environment 34. The man made structures in urban environment 30 may comprise one or more low rise structures, wherein a low rise structure may have no more than four stories. The man made structures in urban environment 30 may comprise one or more high rise structures, wherein a high rise structure may have more than four stories. The structures in the suburban and/or rural environments 32, 34 may comprise one or more low rise structures. For example, urban environment 30 may comprise multiple high-rise office buildings, multiple high rise apartment buildings, and/or one or more low rise restaurants. Rural environment 34 may comprise a single one floor farmhouse.

Returning to FIG. 2, infrastructure and/or man made structures in urban, suburban, and/or rural environments 30, 32, 34 may comprise waste management facilities (e.g., landfill 42), public utilities infrastructure (e.g., power plant 44), wired and/or wireless communications infrastructure (e.g., cell phone tower 46), cultural venues (e.g., stadium 48), parks 50, transportation infrastructure (e.g., roads 52), other infrastructure, and/or other man made structures.

Waste management facilities may comprise trash bins, a trash collection sub-station, a landfill, and/or other waste management facilities. Waste management facilities may be located in the urban 30, suburban 32, and/or rural 34 environments depending on user configuration requirements. The density of waste management facilities may decrease moving from urban environment 30, to suburban environment 32, to rural environment 34. For the present disclosure it is contemplated that trash collection sub-stations may be more commonly located in urban environment 30 and/or suburban environment 32. It is also contemplated that a landfill may be located more commonly in suburban environment 32, and/or rural environment 34.

Public utilities infrastructure may comprise water pipes, a water treatment facility, a water pumping facility, sewer pipes, a sewer treatment facility, a power generation facility, power transmission equipment, and/or other public utilities infrastructure. Public utilities infrastructure may be located in the urban 30, suburban 32, and/or rural 34 environments depending on user configuration requirements. The density of public utilities infrastructure may decrease moving from urban environment 30, to suburban environment 32, to rural environment 34. Public utilities infrastructure may be integrated into urban 30, suburban 32, and/or rural 34 environments as it may be in a typical urban/suburban/rural region. For example, power lines in a rural region may be strung between towers. In an urban region power lines may be buried underground. For the present disclosure it is contemplated that water pipes, a water treatment facility, a water pumping facility, sewer pipes, a sewer treatment facility, and/or power transmission may be more commonly located in urban environment 30 and/or suburban environment 32. It is also contemplated that a power generation facility may be located more commonly in suburban environment 32, and/or rural environment 34. Rural environment 34 may also comprise additional utilities infrastructure such as, for example, a well, a septic tank, and/or other utilities infrastructure.

Public utilities infrastructure may comprise wires, pipes, and/or other methods of transporting power, water, gas, and/or other utilities throughout test facility 10. The wires, pipes, and/or other methods of transport may run under, through (e.g., in the walls), between (e.g., wires strung between buildings), over (e.g., power lines between towers), and/or in other locations with respect to the structures 12 of test facility 10.

Hard-wired and/or wireless telecommunications infrastructure may comprise transmission and/or reception equipment for television, phone, radio internet, and/or other telecommunications infrastructure. For example, telecommunications infrastructure may comprise broadcast radio/television transmitters and/or towers, commercial radio transmission equipment, wireless microwave cellular telephone infrastructure, overhead and/or underground wiring for phone, television, and/or other services, and/or other infrastructure. Telecommunications infrastructure may be located in the urban 30, suburban 32, and/or rural 34 environments depending on user configuration requirements. The density of telecommunications infrastructure may decrease moving from urban environment 30, to suburban environment 32, to rural environment 34. For the present disclosure it is contemplated that telecommunications infrastructure will be integrated into urban 30, suburban 32, and/or rural 34 environments as it may be in a typical urban/suburban/rural region. For example, in urban areas a cell phone tower may be installed on the roof of a building. In suburban and/or rural areas, cell phone towers may be built as a free standing structure. Test facility 10 may be configured to adjust bandwidth, frequency, telecom protocol (e.g., GSM, CDMA), and/or other aspects of the telecommunications infrastructure to simulate legacy meshed networks, both domestic and global.

It is to be understood that the structures, systems, infrastructure, and/or other components of environments 14 combine to form an aggregate (simultaneous, omni-directional, immersive) electromagnetic environment indoors and/or outdoors in the test facility. The aggregate electromagnetic environment may be used for testing electronic communication (indoors and/or outdoors) techniques, navigation sensing, military targeting, and/or for other purposes. For example, power lines, transformers, communications towers and/or transmitters, computers, refrigerators, air conditioners (electric motors), microwaves, electrical wiring, plumbing, signs, fences, cars, and or other components of environments 14 may comprise noise/clutter sources that affect the electromagnetic spectrum and electronic communication. Insulation, metal buildings, thick brick and mortar structures, metal screens, reinforcing steel in concrete, pipes, windows, signs, doors, and/or other components of environments 14 may comprise attenuators and/or reflectors that may cause path loss, multipathing, scatter, and/or other effects during electronic communication. Cars, windows, building materials, fences, walls, etc. may absorb and/or reflect electronic communication in the test facility.

The urban 30 and/or suburban 32 environments may comprise cultural venues. The cultural venues may comprise one or more of a museum, a stadium, a zoo, a concert venue and/or another cultural venue. For the present disclosure it is contemplated that rural environment 34 may contain no cultural venues.

The infrastructure in the urban 30 and/or suburban 32 environments may comprise one or more city parks. A city park may comprise one or more of an open grass field, trees, a pool, a playground, a gymnasium, and/or other features of a park. For the present disclosure it is contemplated that rural environment 34 may contain no parks.

Figure 5:
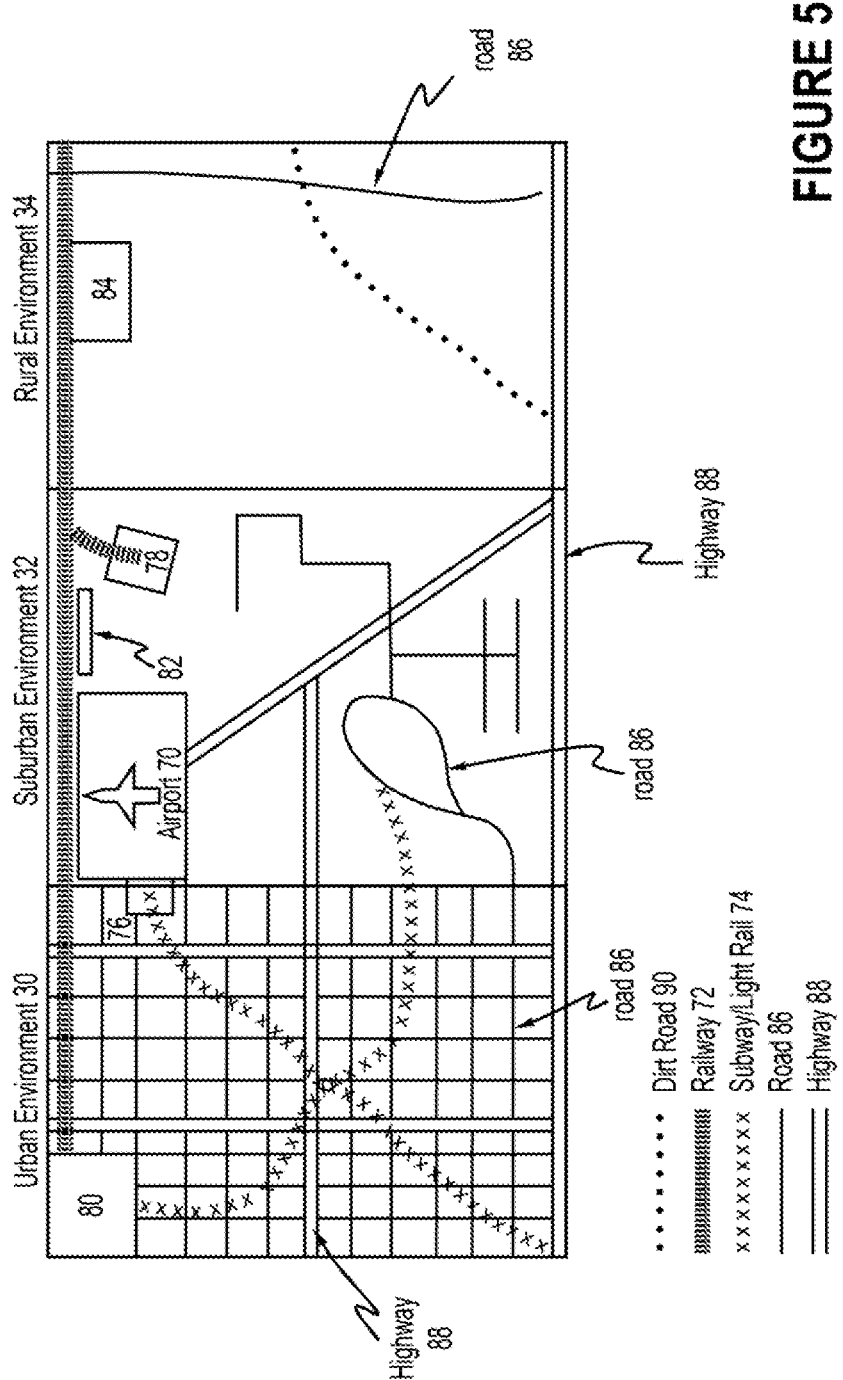
FIG. 5 describes the transportation network in an urban, a suburban, and a rural environment.

FIG. 5 depicts transportation infrastructure in the urban 30, suburban 32, and rural 34 environments. Transportation infrastructure may comprise an airport 70, a railway network 72, a subway/light rail system 74, an automotive transport network, and/or other transportation infrastructure.

Airport 70 may comprise one or more terminals, runways, terminal gates, check in areas, jet ways, a baggage handling system, and/or other features. Airport 70 may comprise a subway/light rail connecting station 76. For the present disclosure it is contemplated that the airport may be located in the urban 30 and/or suburban 32 environments.

Railway network 72 may comprise one or more train tracks, one or more train stations, one or more switching yards, and/or other features. Railway network 72 may be configured to carry passenger and/or freight trains. A switching yard 78 may be located in urban environment 30 and/or suburban environment 32. Train stations may comprise larger passenger transit hubs 80 connecting subway/light rail 74 with railway 72 in urban environment 30, commuter based platforms in suburban environment 32, and/or regional stations in rural environment 34. For the present disclosure it is contemplated that the track density and/or the size and/or quantity of stations decrease moving from urban 30, to suburban 32, to rural 34 environments.

Subway/light rail system 74 may comprise above ground and/or underground railway tracks and above ground and/or underground passenger loading/unloading stations. The stations may be accessible from ground level for passenger transportation to different locations in the urban, and/or suburban environments 30, 32. The density of subway/light rail system lines may be heaviest in urban environment 30 but may extend into suburban environment 32 (e.g., to the airport).

The automotive transportation network may comprise a road network 86 and/or a highway network 88. The automotive transportation network may comprise asphalt roads/highways, concrete roads/highways, dirt roads, gravel roads, sand roads, guard rails, curbs, bridges, autos, trucks, and/or other components. The automotive transportation network may comprise a vehicle to vehicle (V2V) and/or a vehicle to infrastructure (V2I) test bed.

Road network 86 may comprise, for example, roads, intersections, automated traffic guidance, stop signs, parking spaces, traffic cameras and/or other components of a road network. Highway network 88 may comprise one or more of above ground multi lane roadways, underground multi lane roadways, highway on ramps, highway on ramp metering lights, highway off ramps, toll plazas, highway to highway transition ramps, overpasses, underpasses, and/or other components of a highway network.

The automotive transportation network in suburban environment 32 may be less dense than the automotive transportation network in urban environment 30. The automotive transportation network in rural environment 34 may be less dense than the automotive transportation network in suburban environment 32. The automotive transportation network density may comprise one or more of number of roads per given land area, number of lanes per road, number of highways per given land area, number of lanes per highway, number of road intersections per given land area, number of highway intersections per land area, number of parking spaces per land area, amount of automated traffic guidance per given land area, and/or other measures of density.

Returning to FIG. 2, other infrastructure and/or man made structures in urban, suburban, and/or rural environments 30, 32, 34 may comprise test tracks (road course and/or off road), mining/quarrying facilities, structures and/or infrastructure for military exercises, infrastructure for agricultural development, various power generation facilities (e.g., nuclear, coal burning, wind turbines, solar), reactor technology and/or infrastructure (e.g., reactor safety systems, reactor security, and/or other technologies), resource development infrastructure (e.g., water desalinization), infrastructure for testing perimeter security (e.g., sovereign border security), and/or other infrastructure. A user may decide on the appropriate environment(s) 30, 32, 34 (e.g., urban, suburban, rural) to implement additional infrastructure and/or man made structures (e.g., the structures listed above).

Power generation and/or resource development facilities (e.g., a water desalinization plant) may be configured to supply power and/or other resources (e.g., water) to test facility 10. The primary power plant and/or other resource development facilities configured to supply power, water, and/or other resources to test facility 10 may change over time through newly built, reconfigured, and/or other experimental power generation facilities (e.g., geothermal, solar, wind, nuclear.) Test facility 10 may be configured with production, distribution, and/or supply systems for utility grade service delivery on the power, water, and/or other utility grids of test facility 10. Excess energy, water, and/or other resources produced may become available for wholesale delivery to the public utility system outside test facility 10. Test facility 10 may be configured to receive resources (e.g., power, water) from the public utility system outside test facility 10.

A water desalinization plant included as part of test facility 10 may be configured to operate one or more desalinization processes comprising one or more of reverse osmosis, thermal evaporation, ion exchange, forward osmosis, and/or other operations.

Figure 6:
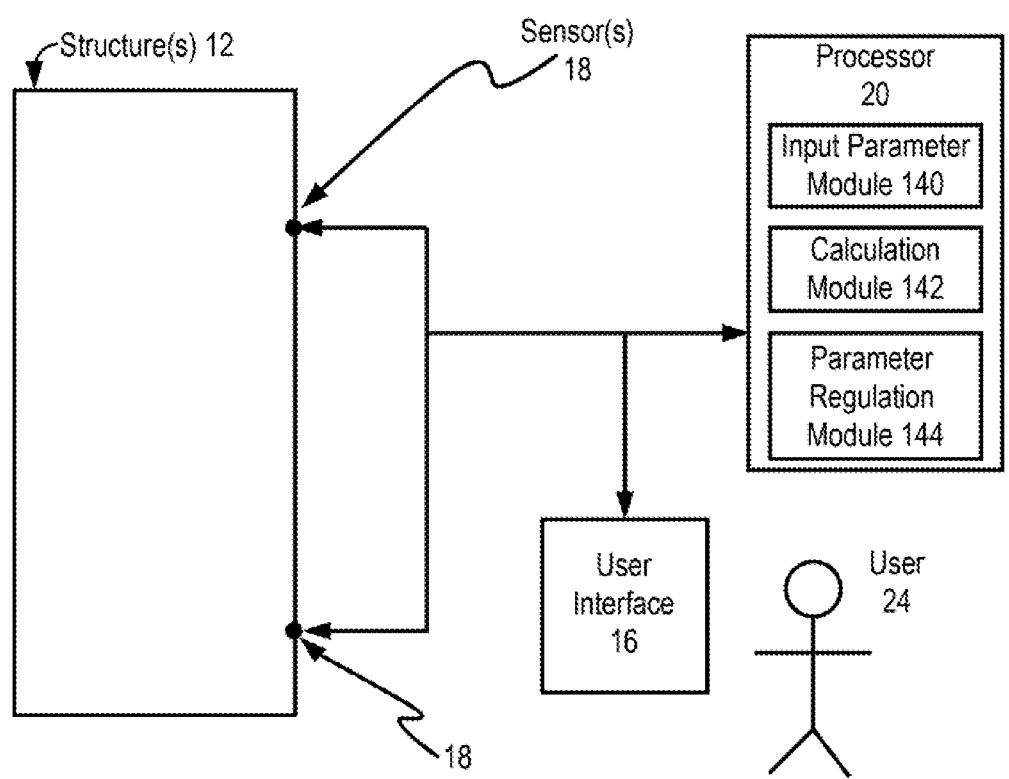
FIG. 6 is a schematic representation of a structure, sensors, a processor, a user interface, and a user in the test facility.

As shown in FIG. 6, user interface 16 is configured to provide an interface between processor 20 and user 24 through which user 24 may provide information to and receive information from processor 20. This enables data, results, and/or instructions and any other communicable items, collectively referred to as "information," to be communicated between user 24 and one or more of processor 20, structure(s) 12, and/or sensors 18. Examples of interface devices suitable for inclusion in user interface 16 include a keypad, buttons, switches, a keyboard, knobs, levers, a display screen, a touch screen, speakers, a microphone, a printer, and/or other interface devices. In one implementation, user interface 16 includes a plurality of separate interfaces. In one implementation, user interface 16 includes at least one interface that is provided integrally with structure(s) 12.

It is to be understood that other communication techniques, either hard-wired or wireless, are also contemplated by the present disclosure as user interface 16. For example, the present disclosure contemplates that user interface 16 may be voice activated. In this example, information indicating one or more demographic input parameters may be input into processor 20 by speaking. Other exemplary input devices and techniques adapted for use with processor 20 as user interface 16 include, but are not limited to, an RS-232 port, RF link, an IR link, modem (telephone, cable or other). In short, any technique for communicating information with processor 20 is contemplated by the present disclosure as user interface 16.

Figure 7:
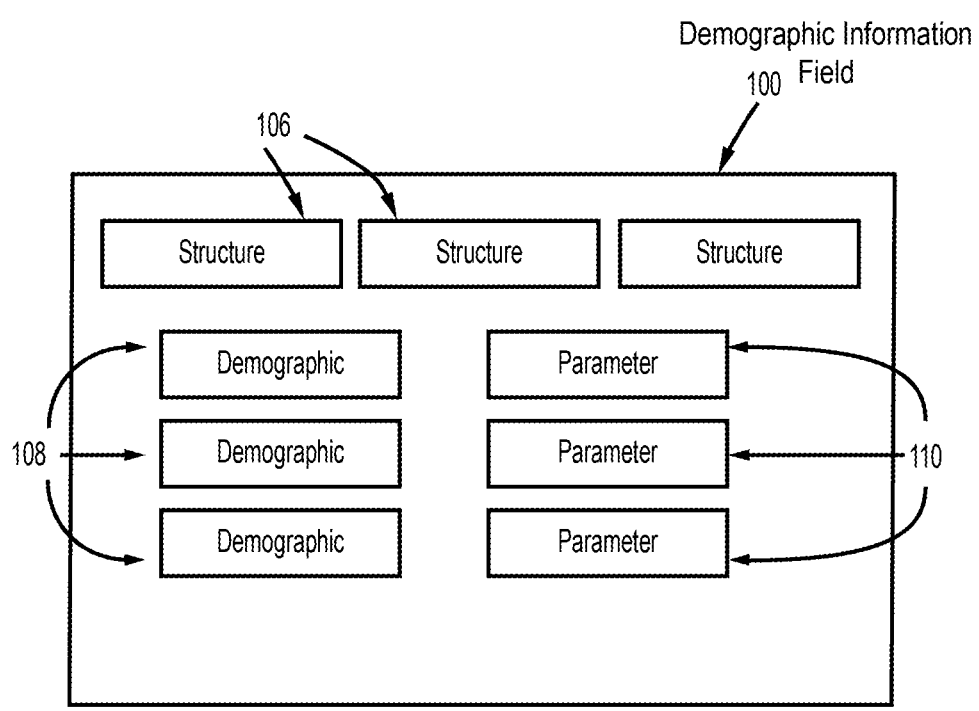
FIG. 7 presents a demographic information field of the user interface.
Figure 8:
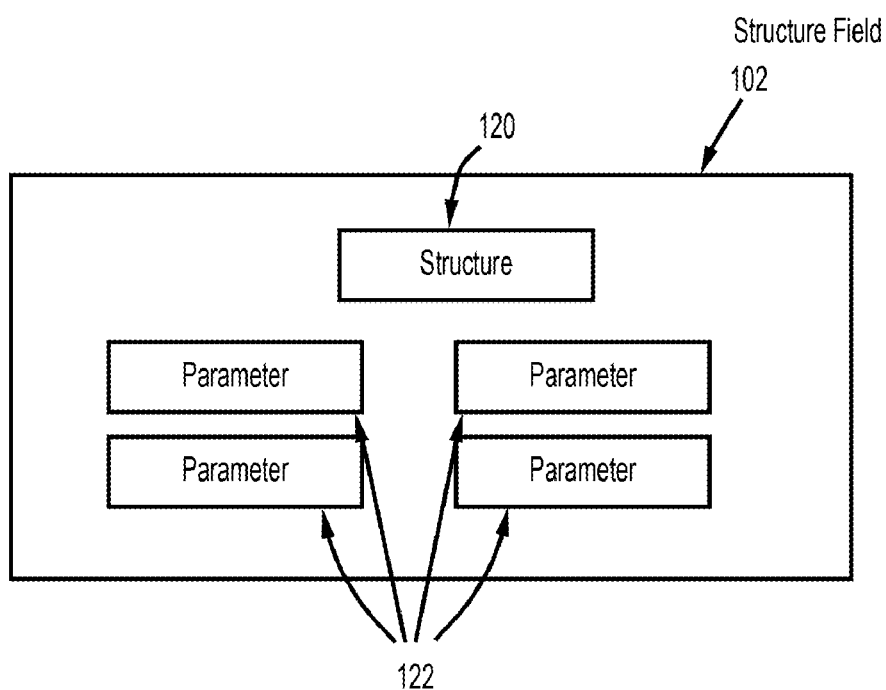
FIG. 8 presents a structure field of the user interface.
Figure 9:
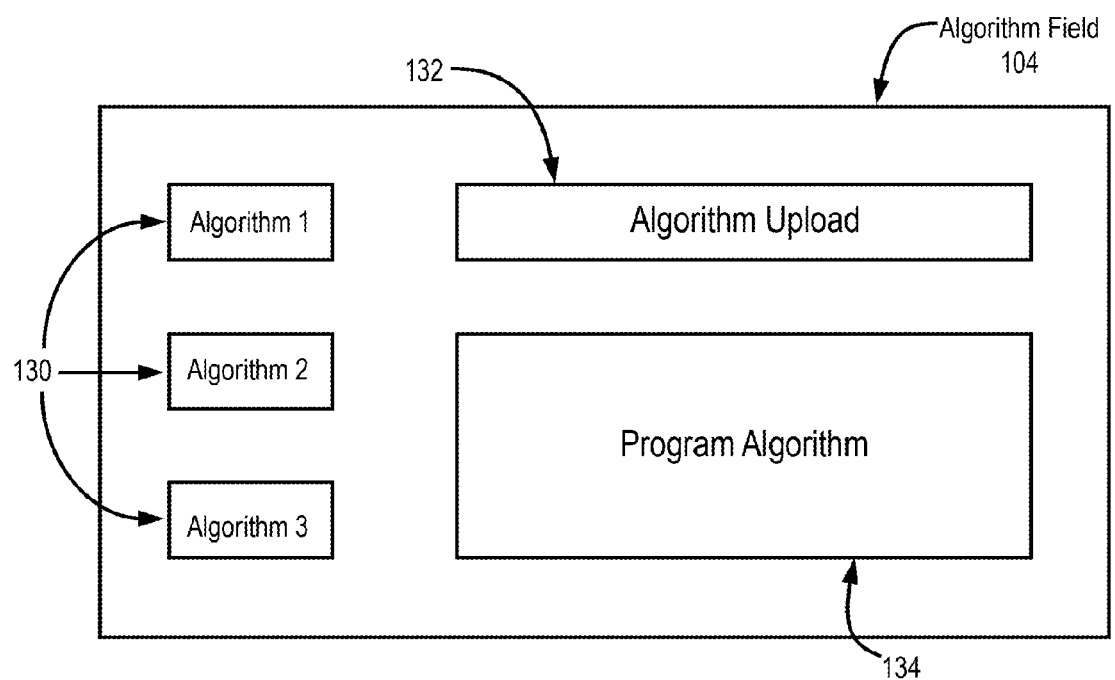
FIG. 9 presents an algorithm field of the user interface.

FIGS. 7-9 present different views of user interface 16. User interface 16 may comprise a demographic information field 100, a structure field 102, an algorithm field 104 and/or other fields. Demographic information field 100 is shown in FIG. 7. Structure field 102 is shown in FIG. 8. Algorithm information field 104 is shown in FIG. 9. The fields of user interface 16 may be configured to allow a user to set up, run, and/or monitor a test, evaluation, simulation, and/or other activity according to the user's requirements.

In FIG. 7, demographic information field 100 may be configured to receive entry and/or selection by a user of demographics of a population the user desires to simulate. Demographic information field 100 may comprise one or more selectable structures 106, one or more demographic information entry fields 108, one or more structure parameter indicators 110, and/or other fields. Using demographic information field 100, the user may, for example, select three different structures for participation in a simulation. The user may enter demographic information about the users of each structure and then view the resulting parameters. Conversely, the user may enter parameter information for each structure and then view the resulting demographic information.

In FIG. 8, structure Field 102 may be configured to receive entry and/or selection by the user of parameter control information related to the structure(s) the user desires to evaluate and/or simulate, and/or view the parameter information on user interface 16. For example, the user may specify an internal structure temperature set point of 72° F. in a specific office building and/or an internal structure temperature set point of 78° F. in a residential house. Structure field 102 may comprise a structure indicator 120, one or more structure parameter indicators 122, and/or other fields.

In FIG. 9, algorithm information field 104 may be configured to receive entry and/or selection of algorithms for use during simulation. Algorithm information field 104 may comprise one or more selectable algorithms 130, one or more uploaded algorithms, one or more programmed algorithms, and/or other algorithms. User selected algorithms may be used by processor 20 (not shown) for simulation calculations.

Returning to FIG. 6, one or more sensors 18 may be configured to generate one or more output signals conveying information related to ambient conditions in and/or around man made structures, facility wide control parameters, structure component control parameters, structure performance, and/or other parameters. For example, smart grid sensors may generate output signals conveying information related to demand response, peak load shaving, synchrophasors, security of the home area network for smart appliances, interface points to the smart grid, RF interference, system integrity, data privacy, and/or other output signals. Output signals generated by sensors 18 may be utilized for one or more of deriving an algorithm, obtaining data to test a hypothesis, returning response information in a control loop feedback mechanism (e.g., a PID controller), monitoring a specific variable relative to threshold level(s), and/or other purposes. For example, output signals from ambient condition sensors around the test facility may convey information indicating atmospheric humidity at each sensor location. A user may program a structure component control parameter calculation algorithm to incorporate location based atmospheric humidity information (e.g., an office building structure located in an area of higher humidity may require more power to run the air conditioner to remove the humidity for the comfort of office workers).

Ambient condition output signals may convey information related to the atmospheric conditions surrounding a sensor. Ambient conditions may comprise one or more of temperature, humidity, pressure, air quality, airflow, wind velocity, light level and/or other ambient conditions. For example, ambient conditions information may be utilized to study the effects man made structures have on their surrounding environment. A user may desire the level of sunlight in a given area to remain above or below a threshold level during a certain time of day. Sunlight levels may be compared before and after a building a new structure in proximity to sensor 18.

Facility wide control parameters may comprise one or more of mechanical load, electrical load, temperature, humidity, power use, water use, and/or other facility wide control parameters. Signals conveying information related to facility wide control parameters may represent characteristics of an entire population. For example, the combined weight of all vehicles in grid locked traffic on the highway system may comprise facility wide mechanical load information for the highway system. In this example, the sensed load information may be used as input to design an increased load bearing highway overpass.

Structure component control parameters control components in a structure. Structure components may comprise one or more of a heater (gas and/or electric for example), an air conditioner (gas and/or electric for example), household appliances, sinks, showers, phone, faucets, toilets, a garage door opener, electronic devices, lighting (interior and/or exterior), doors (interior and/or exterior), windows (e.g., glass, metal frame, security bars), fans, and/or other structure components. Information related to structure component control parameters may be used in a feedback loop during a simulation. For example, a simulation may require the household stove to operate at a given temperature so the stove gives off heat to its surroundings. Information related to the operating temperature of the stove may be compared to the stove set point so the temperature of the stove may be adjusted if necessary.

Information related to structure performance may comprise information indicating the structure's response to simulated use. The response to simulated use may comprise one or more of energy use, energy use efficiency, heat lost to the environment, heat gained from the environment, structure wear and tear over time, response to electrical load, response to temperature load, response to mechanical load, and/or other information related to the structure's response to simulated use. For example, in an office building structure where the air conditioner is programmed to keep the building at or below a set temperature, sensed energy use by the air conditioner may be an indication of how well the building is insulated and/or how well the building is designed to maximize the effects of air conditioning.

Sensors 18 may include one or more sensors that generate output signals related to one or more parameters indirectly. For example, one or more of sensors 18 may generate an output information based on an operating parameter of structures 12 (e.g., an air conditioning unit motor current, voltage, rotational velocity, and/or other operating parameters), and/or other sensors. Although sensors 18 are illustrated at a location at or adjacent to structures 12, this is not intended to be limiting. The sensors 18 may include sensors disposed in a plurality of locations, such as for example, within structures 12, nearby (but not in contact with) structures 12, underneath structures 12 (e.g., if a structure is a road), and/or other locations.

Continuing with FIG. 6, processor 20 may be configured to provide information processing capabilities in test facility 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 6 as a single entity, this is for illustrative purposes only. In some implementations, processor 20 may include a plurality of processing units. These processing units may be physically located within the same device (e.g., processor 20), or processor 20 may represent processing functionality of a plurality of devices operating in coordination.

As is shown in FIG. 6, processor 20 may be configured to execute one or more computer program modules. The one or more computer program modules may comprise one or more of an input parameter module 140, a calculation module 142, a parameter regulation module 144, and/or other modules. Processor 20 may be configured to execute modules 140, 142, and/or 144 by software; hardware; firmware; some combination of software, hardware, and/or firmware; and/or other mechanisms for configuring processing capabilities on processor 20.

It should be appreciated that although modules 140, 142, and/or 144 are illustrated in FIG. 6 as being co-located within a single processing unit, in implementations in which processor 20 includes multiple processing units, one or more of modules 140, 142, and/or 144 may be located remotely from the other modules. The description of the functionality provided by the different modules 140, 142, and/or 144 described below is for illustrative purposes, and is not intended to be limiting, as any of modules 140, 142, and/or 144 may provide more or less functionality than is described. For example, one or more of modules 140, 142, and/or 144 may be eliminated, and some or all of its functionality may be provided by other ones of modules 140, 142, and/or 144. As another example, processor 20 may be configured to execute one or more additional modules that may perform some or all of the functionality attributed below to one of modules 140, 142, and/or 144.

Input parameter module 140 may be configured to obtain one or more input parameters. The one or more input parameters may be obtained responsive to one or more inputs made by user 24 via user interface 16, output information from sensor(s) 18, and/or other sources. The one or more input parameters may comprise, for example, ambient conditions, fictional weather conditions, time of day, geographic location, the people and/or entity interacting with the structure, the size of entity and/or the number of people interacting with a structure, biographical information about the people interacting with a structure, and/or other input parameters.

Calculation module 142 may be configured to calculate, responsive to the information obtained by input parameter module 140, (i) facility wide control parameters comprising one or more of mechanical load, electrical load, temperature, humidity, power use, water use and/or other parameters, and (ii) structure specific component control parameters, wherein components of a structure may comprise one or more of a heater, an air conditioner, household appliances, sinks, showers, faucets, toilets, electronic devices, lighting, windows, fans and/or other components of a structure. The calculated parameter information may comprise outputs from calculation module 142.

The structure specific component control parameters may be calculated stochastically for each individual structure. For example, calculation module 142 may receive input information from input parameter module 140 describing an urban population of 100,000 people with a specific set of demographics entered by user 24 via user interface 16. Responsive to the input information, calculation module 142 may calculate that a population of that size may use 5,000,000 gallons of water per day. Calculation module 142 may stochastically calculate the fraction of the water used by each individual structure in the urban environment.

In some implementations, calculation module 142 may be configured to perform calculations based on one or more algorithms programmed into calculation module 142, pre-programmed algorithms uploaded by user 24 via user interface 16, algorithms programmed by the user using user interface 16, and/or other algorithms. As an illustration, in the example above, the 5,000,000 gallons of water facility wide control parameter may be calculated based on a pre-programmed algorithm. The stochastic fractional water use calculation for each individual structure may be calculated based on an algorithm programmed by user 24 via user interface 16.

Parameter regulation module 144 may be configured to regulate facility wide and/or structure component control parameters based on output from calculation module 142. Parameter regulation module 144 outputs command signals configured to regulate the operation of facility wide and/or individual structure components. Continuing with the example above, based on results of the stochastic fractional water use calculation, parameter regulation module 144 may output command signals to coordinate operation of sinks, showers, toilets and/or other water using components across the entire facility and/or in an individual structure.

Figure 10:
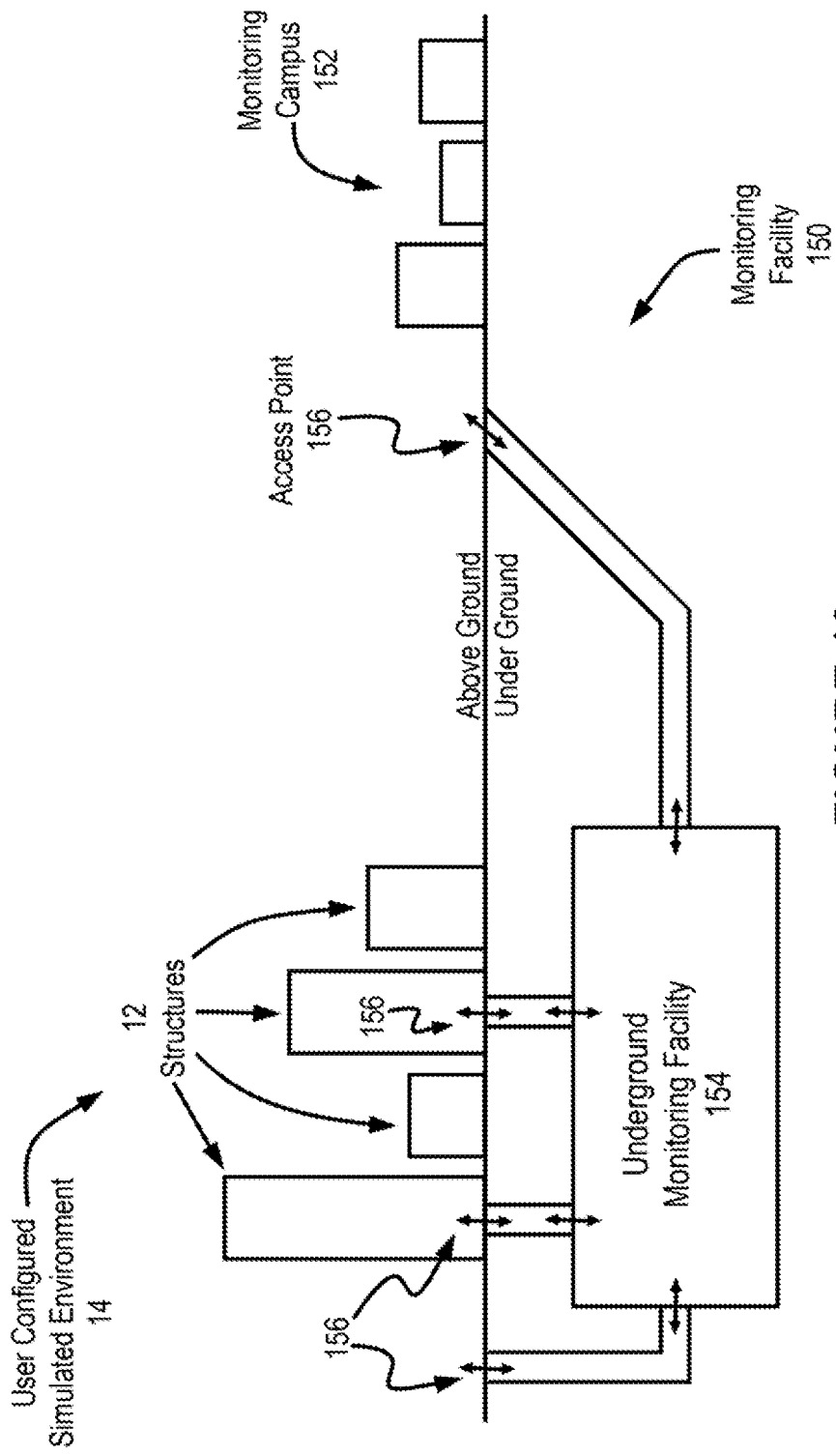
FIG. 10 describes the monitoring facility.

FIG. 10 depicts monitoring facility 150. Monitoring facility 150 may be configured to allow physical, electronic, and/or other monitoring of user configured simulated environments 14, and/or the simulated use of man made structures 12, without interrupting and/or influencing a simulation. The monitoring facility may comprise one or more above ground campuses 152 located away from environment(s) 14, and/or an underground facility 154 located underground below environment(s) 14.

Monitoring may comprise one or more of uploading and/or monitoring input information, monitoring facility wide control parameters, monitoring calculated structure specific component control parameters, monitoring operation/use of structure components, monitoring ambient conditions, and/or other monitoring. The present disclosure contemplates that users of test facility 10 will place test equipment below ground and monitoring equipment above ground. For example, for some tests, users of test facility 10 need not be present above ground in test facility 10 except to place and retrieve sensors. Test facility 10 above ground infrastructure may be configured with common "plug and play" sensor ports and central points for data collection, wherein the data may be transmitted to underground facility 154.

The input information may comprise, for example, one or more of fictional weather conditions, time of day, geographic location, the people and/or entity interacting with the structure(s), the size of entity and/or the number of people interacting with the structure(s), or biographical information about the people interacting with the structure(s). The facility wide control parameters may comprise, for example, one or more of mechanical load, electrical load, temperature, humidity, power use, or water use. Components of a structure may comprise, for example, one or more of a heater, an air conditioner, household appliances, sinks, showers, faucets, toilets, electronic devices, lighting, windows, fans, and/or other components.

Underground facility 154 may be configured so as to be physically and/or electronically (wired and/or wirelessly) interconnected with the operating infrastructure and/or structures 12 above. Underground facility 154 may be configured to host and/or manage all the systems operating the above ground structures, infrastructure, and/or other aspects of environments 14 (e.g., utilities, security, maintenance, data collection, test monitors, etc.). Underground facility 154 may be configured to host and/or manage analytic and/or test laboratories interacting with the above ground structures, infrastructure, and/or other aspects of environments 14 in their simulation, test, and/or evaluation activities.

Underground facility 154 may be configured to host and/or manage core and non-core resource production activities (e.g., data centers, power generation, water purification, etc.) that generate value independent of the use of the above ground structures, infrastructure, and/or other aspects of environments 14. Underground facility 154 may be connected to the public water, electrical, telecommunications, and/or other public utility grids and may be configured to channel excess resource production from above ground test systems onto the public grid.

Underground facility 154 may comprise an electromagnetic pulse (EMP) hardened, electromagnetic interference (EMI) protected (two-way), underground interconnected series of rooms and/or passageways with above ground access points 156 distributed throughout the simulated environments and/or man made structures of test facility 10. For example, the underground monitoring facility may comprise one or more of a room, a tunnel, a hallway, an office, a conference room, a laboratory facility, a clean room, a computing facility, telecommunications infrastructure, a parking garage, a heavy lift elevator system for moving vehicles and/or equipment, for example, a cafeteria for staff, and/or other facilities. Underground facility 154 may comprise one or more anechoic chambers configured for frequency broadcast vacuum analysis wherein the one or more chambers are isolated from frequency noise from the legacy systems located above ground in environments 10. Underground facility 154 may be accessible from above ground via one or more access points configured so as not interrupt and/or influence a simulation during use of the access point.

Above ground campus 152 may be configured to serve as an operating and distribution center for power, water, telecommunications, and/or other utilities. Campus 152 may be configured to house test facility 10 administration, user tenants from one or more users testing in test facility 10, and/or other tenants. Above ground monitoring campus 152 may comprise one or more structures housing one or more hallways, offices, conference rooms, conference venues, laboratory facilities, computing facilities, telecommunications infrastructure, parking garages, and/or other facilities. Campus 152 may be configured with high speed, globally interconnected telecommunications connectivity, low cost energy, and/or other utilities. Campus 152 may be located near an interstate highway system and/or near international air terminal access.

Above ground campus 152 may be located away (e.g., 8 kilometers) from user configured simulated environments 14 so as not to interrupt and/or influence a simulation during normal daily use of above ground monitoring campus 152. Test facility 10 may be configured to generate its own RF signature through its own wireless architecture, broadcasting within test facility 10. Above ground monitoring campus' 152 location away (e.g., 8 kilometers) from user configured simulated environments 14 may permit test facility 10 to qualify for an FCC broadcast waiver.

Underground facility 154, and/or above ground campus 152 may be configured to communicate with each other, environments 14, man made structures 12 in environments 14, and/or outside the test facility wirelessly or via hard-wired connections. Telecommunications may be connected to the public (beyond test facility 10) via secure conduit with dedicated fiber optic links. Underground facility 154 and/or above ground campus 152 may be expandable to match expansion of environments 14 and/or man made structures 12 in environments 14. Underground facility 154 and/or above ground campus 152 may be configured and/or reconfigured to meet user specifications. The various systems operating in underground facility 154, above ground campus 152, environments 14, and/or other components of test facility 10 may be controlled by one central system operated from underground monitoring facility 154.

Figure 11:
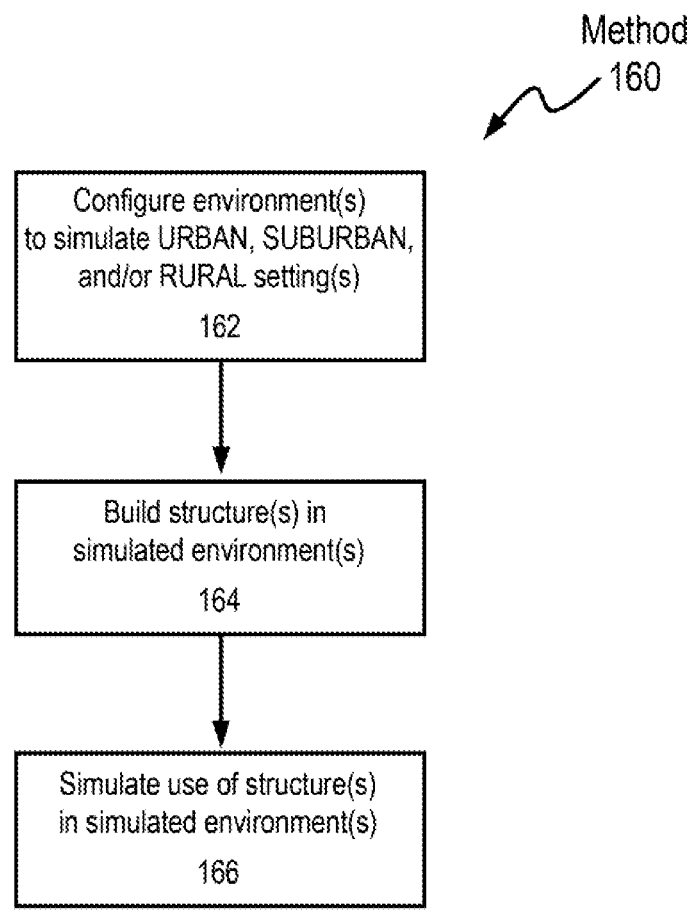
FIG. 11 is a method for simulating use of a structure in a simulated environment.

FIG. 11 illustrates a method 160 of simulating use of a man made structure in a simulated environment. The operations of method 160 presented below are intended to be illustrative. In some implementations, method 160 may be accomplished with one or more additional operations not described, and/or without one or more of the operations discussed. Additionally, the order in which the operations of method 160 are illustrated in FIG. 11 and described below is not intended to be limiting.

In some implementations, method 160 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 160 in response to instructions stored electronically on an electronic storage medium. The one or more processing devices may include one or more devices configured through hardware, firmware, and/or software to be specifically designed for execution of one or more of the operations of method 160.

At an operation 162, one or more environments may be configured to simulate urban, suburban, and/or rural environments. In some implementations, operation 162 is performed by an environment similar to urban environment 30, suburban environment 32, and/or rural environment 34 (shown in FIG. 2 and described herein).

At an operation 164, one or more structures are built in the one or more simulated environments. In some implementations, operation 164 is performed by structures similar to structures 12 (shown in FIG. 1 and described herein).

At an operation 166, use of the one or more structures in the one or more simulated environments is simulated. In some implementations, operation 166 is performed by a processor similar to processor 20 (shown in FIG. 1 and described herein).

Figure 12:
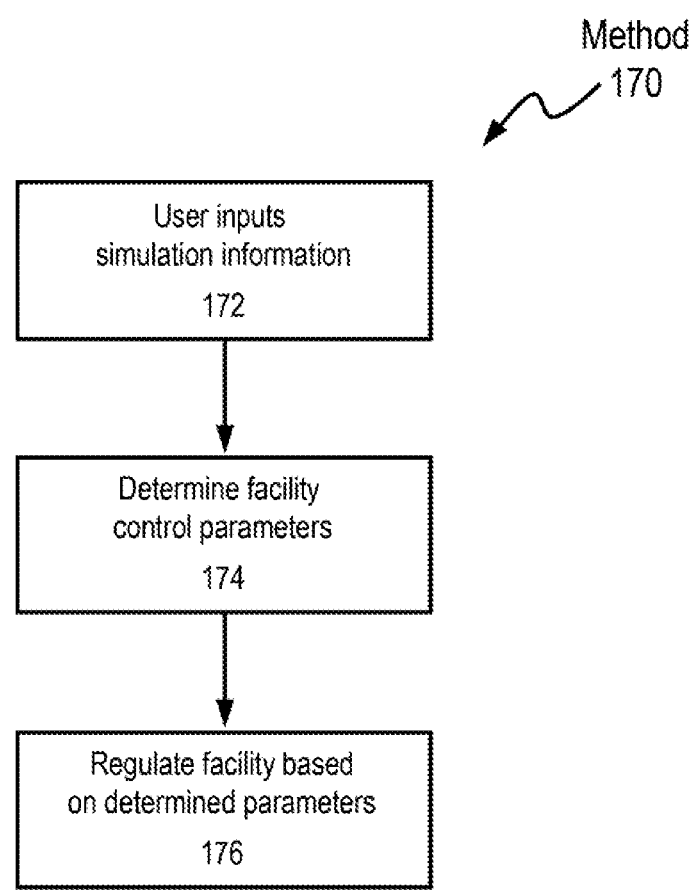
FIG. 12 is a method for regulating the test facility based on determined parameters.

FIG. 12 illustrates a method 170 of regulating use of a test facility. The operations of method 170 presented below are intended to be illustrative. In some implementations, method 170 may be accomplished with one or more additional operations not described, and/or without one or more of the operations discussed. Additionally, the order in which the operations of method 170 are illustrated in FIG. 12 and described below is not intended to be limiting.

In some implementations, method 170 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 170 in response to instructions stored electronically on an electronic storage medium. The one or more processing devices may include one or more devices configured through hardware, firmware, and/or software to be specifically designed for execution of one or more of the operations of method 170.

At an operation 172, a user may input simulation information. The input information may comprise, for example, one or more of ambient conditions, fictional weather conditions, time of day, geographic location, the people and/or entity interacting with a man made structure(s), the size of entity and/or the number of people interacting with the structure(s), biographical information about the people interacting with the structure(s), and/or other input information. In some implementations, operation 172 is performed by a user and/or a user interface similar to user 24 and/or user interface 16 (shown in FIG. 1 and described herein).

At an operation 174, facility control parameters may be determined. The facility wide control parameters may comprise, for example, one or more of mechanical load, electrical load, temperature, humidity, power use, water use, and/or other parameters. In some implementations, operation 174 may be performed by a processor similar to processor 20 (shown in FIG. 1 and described herein).

At an operation 176, the test facility may be regulated based on the determined control parameters. Regulating the test facility based on the control parameters may simulate use of man made structures in a simulated environment(s) per user input(s). In some implementations, operation 176 may be performed by a processor similar to processor 20 (shown in FIG. 1 and described herein).

Figure 13:
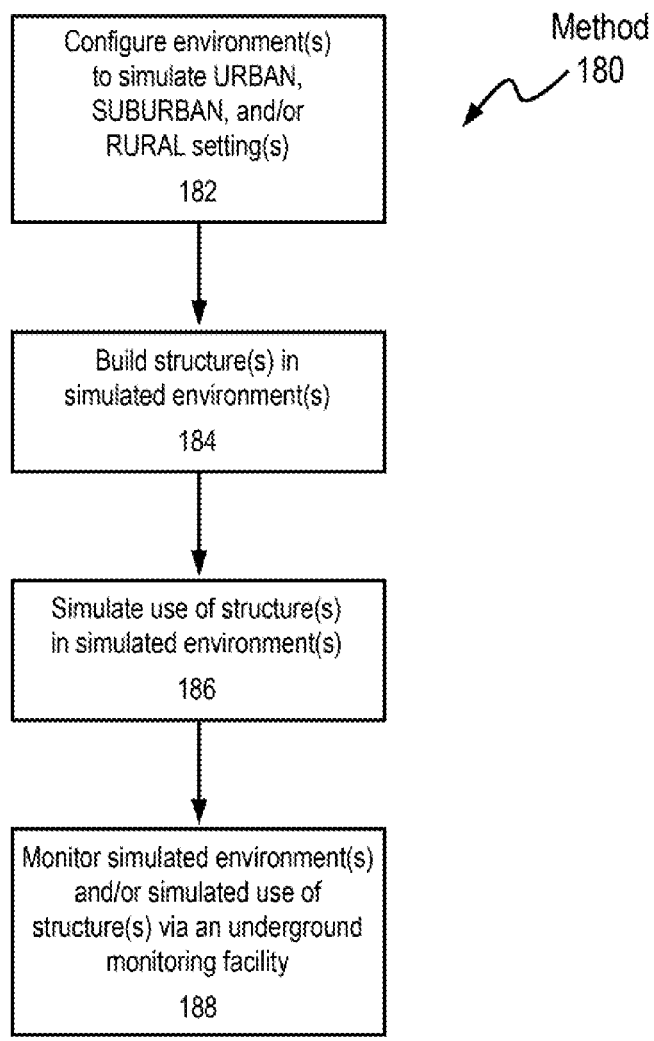
FIG. 13 is a method to monitor simulated environments and/or simulated use of structures via an underground monitoring facility.

FIG. 13 illustrates a method 180 of simulating use of a man made structure in a simulated environment and monitoring the simulated environment and/or the simulated use of man made structure(s) in the simulated environment(s). The operations of method 180 presented below are intended to be illustrative. In some implementations, method 180 may be accomplished with one or more additional operations not described, and/or without one or more of the operations discussed. Additionally, the order in which the operations of method 180 are illustrated in FIG. 13 and described below is not intended to be limiting.

In some implementations, method 180 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 180 in response to instructions stored electronically on an electronic storage medium. The one or more processing devices may include one or more devices configured through hardware, firmware, and/or software to be specifically designed for execution of one or more of the operations of method 180.

At an operation 182, one or more environments may be configured to simulate urban, suburban, and/or rural environments. In some implementations, operation 182 may be performed by an environment similar to urban environment 30, suburban environment 32, and/or rural environment 34 (shown in FIG. 2 and described herein).

At an operation 184, one or more structures may be built in the one ore more simulated environments. In some implementations, operation 184 may be performed by structures similar to structures 12 (shown in FIG. 1 and described herein).

At an operation 186, use of the one or more structures in the one or more simulated environments may be simulated. In some implementations, operation 186 may be performed by a processor similar to processor 20 (shown in FIG. 1 and described herein).

At an operation 188, the one or more simulated environments and/or the use of the one or more structures in the one or more simulated environments may be monitored. Monitoring may comprise uploading and/or monitoring input information, monitoring facility wide control parameters, and/or monitoring stochastically calculated structure specific component control parameters. In some implementations, operation 188 may be performed by monitoring facility 150 (shown in FIG. 10 and described herein).

Figure 14:
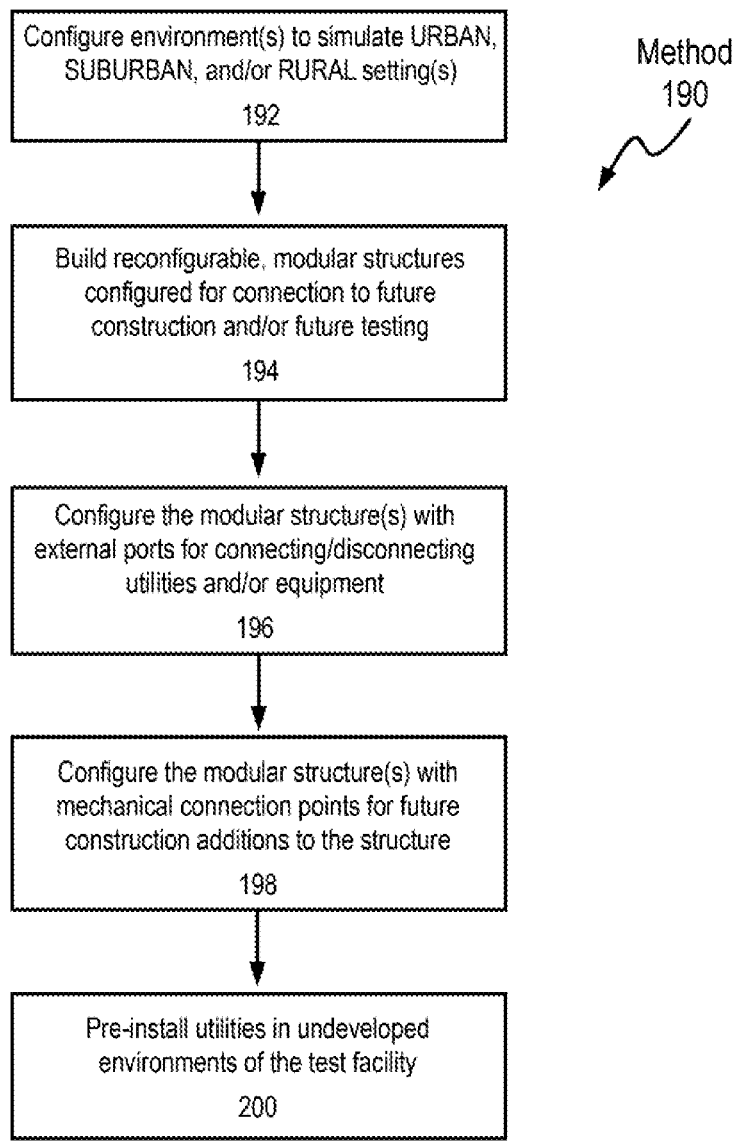
FIG. 14 is a method for building reconfigurable modular structures.

FIG. 14 illustrates a method 190 of building reconfigurable structures in a simulated environment. The operations of method 190 presented below are intended to be illustrative. In some implementations, method 190 may be accomplished with one or more additional operations not described, and/or without one or more of the operations discussed. Additionally, the order in which the operations of method 190 are illustrated in FIG. 14 and described below is not intended to be limiting.

At an operation 192, one or more environments may be configured to simulate urban, suburban, and/or rural environments. In some implementations, operation 192 may be performed by an environment similar to urban environment 30, suburban environment 32, and/or rural environment 34 (shown in FIG. 2 and described herein).

At an operation 194, a user may build reconfigurable, modular structures configured for connection to future construction and/or future testing. In some implementations, operation 194 may be performed by structure(s) similar to structures 12 (shown in FIG. 1 and described herein).

At an operation 196, the reconfigurable, modular structures may be configured with external ports for connecting/disconnecting utilities and/or other equipment. In some implementations, operation 196 may be performed by structure(s) similar to structure(s) 12 (shown in FIG. 1 and described herein).

At an operation 198, the reconfigurable, modular structures may be configured with mechanical connection points for future construction additions to the structure, and/or other future construction. In some implementations, operation 198 may be performed by structure(s) similar to structure(s) 12 (shown in FIG. 1 and described herein).

At an operation 200, utilities may be pre-installed in undeveloped environments of the test facility. Pre-installed utilities may comprise one or more of water, power, or electricity. In some implementations, operation 182 may be performed by an environment similar to urban environment 30, suburban environment 32, and/or rural environment 34 (shown in FIG. 2 and described herein).

Although the system(s) or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A full scale uninhabited test facility configured for building, and evaluating man made structures, the test facility comprising:
   user configurable uninhabited environments configured to:
   simulate settings in which man made infrastructure and structures are built; and
   simulate use of man made infrastructure and structures in the simulated settings;
   the user configurable environments comprising:
   an urban environment configured to simulate infrastructure and structures in a city;
   a suburban environment configured to simulate infrastructure and structures around a city; and
   a rural environment configured to simulate infrastructure and structures in non urban or suburban areas; and
   an underground monitoring facility configured to facilitate monitoring the infrastructure and structures including simulated use of the infrastructure and structures in the urban environment, the suburban environment, and the rural environment without interrupting a simulation,
   wherein monitoring comprises:
   uploading input information for the simulation, the input information indicating: fictional weather conditions; a time of day; a geographic location; a number of people interacting with the infrastructure and structures in the urban, suburban, and rural environments; and biographical information about the people interacting with the infrastructure and structures in the urban, suburban, and rural environments;
   monitoring facility wide control parameters, the facility wide control parameters comprising a mechanical load, an electrical load, a temperature, a humidity, power use, and water use; and
   monitoring stochastically calculated structure specific component control parameters, wherein components of a structure comprise a heater, an air conditioner, household appliances, sinks, showers, faucets, toilets, electronic devices, lighting, windows, and fans.

2. The test facility of claim 1, wherein the structures in the urban environment comprise:
   an urban structure density, wherein structure density is the combined interior square footage of structures per given land area.

3. The test facility of claim 2, wherein a suburban structure density is lower than the urban structure density.

4. The test facility of claim 3, wherein a rural structure density is lower than the suburban structure density.

5. The test facility of claim 4, wherein structure density varies geographically across the urban, suburban, and/or rural environments.

6. The test facility of claim 1, wherein the structures in the urban, suburban, and rural environments comprise:
   structure dimensional variation, wherein structure height, width, and/or depth vary from one structure to the next.

7. The test facility of claim 6, wherein the structures in the urban environment comprise one or more of:
   one or more low rise structures, wherein a low rise structure is no more than four stories tall; or
   one or more high rise structures, wherein a high rise structure is more than four stories tall.

8. The test facility of claim 6, wherein the structures in the suburban and/or rural environments comprise one or more low rise structures, wherein a low rise structure comprises a structure no more than four stories tall.

9. The test facility of claim 1, wherein infrastructure in the urban environment comprises transportation infrastructure, wherein the transportation infrastructure comprises:
   a subway system, wherein the subway system comprises underground railway tracks and above ground/underground passenger loading/unloading stations accessible from street level for passenger transportation to different locations in the urban environment; and
   an automotive transportation network, wherein the automotive transportation network comprises:
      a road network, wherein the road network comprises one or more of roads, intersections, automated traffic guidance, stop signs, parking spaces, or traffic cameras; and
      a highway network, wherein the highway network comprises one or more of above ground multi lane roadways, underground multi lane roadways, highway on ramps, highway on ramp metering lights, highway off ramps, toll plazas, or highway to highway transition ramps.

10. The test facility of claim 1, wherein infrastructure in the suburban environment comprises transportation infrastructure, wherein the transportation infrastructure comprises:
    an automotive transportation network, wherein the automotive transportation network comprises:
       a road network, wherein the road network comprises one or more of roads, intersections, automated traffic guidance, stop signs, parking spaces, or traffic cameras; and
       a highway network, wherein the highway network comprises one or more of above ground multi lane roadways, underground multi lane roadways, highway on ramps, highway on ramp metering lights, highway off ramps, toll plazas, automated traffic guidance, or highway to highway transition ramps.

11. The test facility of claim 10, wherein the automotive transportation network in the suburban environment is less dense than an automotive transportation network in the urban environment, and wherein automotive transportation network density comprises one or more of number of roads per given land area, number of lanes per road, number of highways per given land area, number of lanes per highway, number of road intersections per given land area, number of highway intersections per land area, number of parking spaces per land area, or amount of automated traffic guidance per given land area.

12. The test facility of claim 1, wherein the infrastructure in the rural environment comprises transportation infrastructure, wherein the transportation infrastructure comprises:
    an automotive transportation network, wherein the automotive transportation network comprises one or more of paved roads, dirt roads, intersections, parking spaces or automated traffic guidance.

13. The test facility of claim 12, wherein the automotive transportation network in the rural environment is less dense than an automotive transportation network in the suburban environment, and wherein automotive transportation network density comprises one or more of number of roads per given land area, number of lanes per road, number of highways per given land area, number of lanes per highway, number of road intersections per given land area, number of highway intersections per land area, number of parking spaces per land area, or amount of automated traffic guidance per given land area.

14. The test facility of claim 1, wherein the infrastructure in rural areas comprises:
    one or more open land tracts, wherein an open land tract comprises:
       an open area of land between man made structures; and
       one or more of farmland, land for grazing cattle, or undeveloped land containing no man made structures.

15. The test facility of claim 1, wherein the structures in the urban environment comprise cultural venues, wherein the cultural venues comprise one or more of a museum, a stadium, a zoo, or a concert venue.

16. The test facility of claim 1, wherein the infrastructure in the urban and/suburban environments comprises a park, and wherein the park comprises one or more of an open grass field, trees, a pool, a playground, or a gymnasium.

17. The test facility of claim 1, wherein the infrastructure in the urban, suburban, and/or rural environments simulates a typical aggregate electromagnetic environment.

18. The test facility of claim 1, wherein the underground monitoring facility comprises an interconnected series of rooms housing monitoring equipment, and/or passageways with above ground access points distributed throughout the environments of the test facility, such that a user located in the underground monitoring facility monitors the infrastructure and structures in the environments and the simulated use of the infrastructure and structures without interrupting a simulation via the monitoring equipment.

19. The test facility of claim 1, wherein the underground monitoring facility is accessible from above ground via one or more access points configured so as not interrupt a simulation during use of the access point.

20. The test facility of claim 1, wherein the underground monitoring facility is configured to communicate with the infrastructure and structures in the environments, and outside the test facility wirelessly or via wires.

21. The test facility of claim 1, wherein the underground monitoring facility comprises three or more of a room, a tunnel, a hallway, an office, a conference room, a laboratory facility, a computing facility, or telecommunications infrastructure.

22. The test facility of claim 1, wherein the underground monitoring facility is expandable to match expansion of the infrastructure and structures in the environments.

* * * * *